United States Patent [19]
Fried

[11] Patent Number: 5,155,278
[45] Date of Patent: Oct. 13, 1992

[54] PROCESS FOR THE OXIDATION OF ALCOHOLS TO ALDEHYDES

[75] Inventor: Herbert E. Fried, Houston, Tex.

[73] Assignee: Shell Oil Company, Houston, Tex.

[21] Appl. No.: 769,077

[22] Filed: Sep. 30, 1991

[51] Int. Cl.⁵ .................. C07C 45/37; C07C 45/32
[52] U.S. Cl. ................... 568/471; 568/426; 568/435; 568/449; 568/470; 568/485
[58] Field of Search ............... 568/426, 449, 470, 471, 568/472, 485, 486, 487, 455, 436, 435

[56] References Cited

U.S. PATENT DOCUMENTS 4,620,033  10/1986  Isshiki et al. .................. 562/519

FOREIGN PATENT DOCUMENTS 5096516  11/1986  Japan .................. 562/519

OTHER PUBLICATIONS

Miyazawa et al., "Oxidation of Benzyl Alcohol with Iron(III) Using Polymers Containing Nitroxyl Radical Structure as a Mediator," J. Polym. Sci., Polym. Chem. Ed., 23(9), 1985, pp. 2487-2494.

Grigor'ev et al., "Participation of Nitroxyl Radical in the Oxidation of Aldehyde and Alcohol Groups in 3-imidazolin-1-oxyls," Izc. AKad. Nauk SSSR, Ser. Khim., (1), 1978, pp. 208-210.

Miyazawa et al., "Oxidation of Benzyl Alcohol with Copper(II) Mediated by a Polymeric Oxoaminium Salt," J. Mol. Catal., 49(1), 1988, 131-134.

Ganem et al., "Biological Spin Labels as Organic Reagents, Oxidation of Alcohols to Carbonyl Compounds Using Nitroxyls", J. Org. Chem., 40(13), 1975, pp. 1998-2000.

Miyazawa et al., "Oxidation of Benzyl Alcohol by Iron-(III) Mediated by Nitroxyl Radical," J. Mol. Catal., 31(2), 1985, pp. 217-220.

Anelli et al., "Fast and Selective Oxidation of Primary Alcohols to Aldehydes or to Carboxylic Acids and of Secondary Alcohols to Ketones Mediated by Oxoammonium Salts under Two-Phase Conditions," J. Org. Chem., 52 (12), pp. 2559-2562.

Inokuchi et al. "A Selective and Efficient Method for Alcohol Oxidations Mediated by N-Oxoammonium Salts in Combination with Sodium Bromite," J. Org. Chem., 1990, 55 pp. 462-466.

Organic Synthesis, vol. 69, p. 212 (1990).

Semmelhack et al. "Oxidation of Alcohols to Aldehydes with Oxygen and Cupric Ion, Mediated by Nitrosonium Ion," J. Amer. Chem. Soc. 1984 106, 3374-3376.

Yamaguchi et al., "Application of Redox System Based on Nitroxides to Organic Synthesis," Pure & Applied Chemistry, vol. 62(2), 1990, pp. 217-222.

*Primary Examiner*—Werren B. Lone
*Attorney, Agent, or Firm*—Pamela J. McCollough

[57] ABSTRACT

A process for the preparation of an aldehyde which comprises reacting the corresponding alkanol with a solubilized stable free radical nitroxide having the formula:

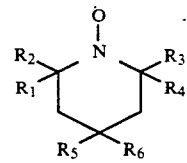

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid and a nonbasic polar solvent, in the presence of an oxidant, for about eight hours or less at a temperature in the range of from about $-10°$ C. to about $25°$ C., and thereafter separating out the aldehyde.

14 Claims, No Drawings

PROCESS FOR THE OXIDATION OF ALCOHOLS TO ALDEHYDES

FIELD OF THE INVENTION

This invention relates to a process for the preparation for the preparation of aldehydes by the oxidation of the corresponding alcohols in the presence of a stable free radical nitroxide, nitric acid, a non-basic polar solvent and an oxidant.

BACKGROUND OF THE INVENTION

It is known to use nitroxyl radicals/oxoammonium salts in the oxidation of primary alcohols to produce aldehydes and acids and secondary alcohols to ketones (*Journal of Organic Chemistry*, vol. 52) (12), pp. 2559–2562 and *Journal of Organic Chemistry*, vol. 55, 1990, p. 462–466).

It is reported in the open literature that primary aliphatic alcohols can be converted to aldehydes in 30–40% yields in presence of catalytic amounts of cuprous chloride, 2,2,6,6,-tetramethylpiperidine-1-oxyl, and atmospheric oxygen (*Journal of American Chemical Society*, 1984, 106, pp. 3374). It is also known that higher yields of aldehydes can be obtained if stoichiometric amounts of cupric or ferric salts are used instead of catalytic amounts of the cuprous salts (*Pure and Applied Chemistry*, vol. 62(2), 1990, pp. 217–222).

OBJECTS OF THE INVENTION

It is an object of this invention to produce aldehydes with high selectivities from alkanols without producing large amounts of other products such as acids and esters.

It has ben found that aldehydes can be produced in high yields and/or with high selectivities by using catalytic amounts of a stable free radical nitroxide, nitric acid and an oxidant.

SUMMARY OF THE INVENTION

This invention relates to a process for the preparation of an aldehyde which comprises reacting the corresponding alkanol with a solubilized stable free radical nitroxide having the formula:

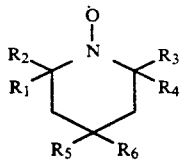

wherein each of $R_1$, $R_2$, $R_3$ and $R_4$ is an alkyl, aryl or heteroatom substituted alkyl group having 1 to about 15 carbon atoms and each of $R_5$ and $R_6$ is alky, hydrogen, aryl or a substituted heteroatom, nitric acid, a non-basic polar solvent and an oxidant, for about eight hours or less at a temperature in the range of about $-10°$ C. to about $25°$ C., and thereafter separating out the aldehyde.

DESCRIPTION OF THE PREFERRED EMBODIMENTS

The present process converts alkanols to the corresponding aldehydes by contacting the alkanol with a solubilized stable free radical nitroixde, nitric acid, a solvent and an oxidant, for about eight hours or less at a temperature in the range of from about 10° C. to about 25° C.

The alkanol reactant suitably comprises one or more alkanols having a carbon number in the range of from about 1 to about 45. An alkanol consisting essentially of primary, mono-alkanols is preferred. Most preferably, the alkanol reactant consists essentially of one or more $C_6$ to $C_{30}$ primary mon-alkanols. Preference can also be expressed for alkanols having from 8 to about 20 carbon atoms, with $C_9$ to $C_{18}$ alkanols considered more preferred about $C_{11}$ to $C_{18}$ alkanols considered most preferred. As a general rule, the carbon chains of the alkanols may be of either branched or linear (straight-chain) structure, although preference further exists for alkanol reactants in which greater than about 50 percent, more preferably greater than about 70 percent and most preferably greater than about 90 percent of the molecules are of linear (straight-chain) carbon structure. In large part, such preferences relate more to the utility and value of the products than to the operability or performance of the process of the invention.

The general suitability of such alkanols as reactants in oxidation reactions is well recognized in the art. Examples of specific alkanols and of commercially available alkanols and alkanol mixtures within this class are also well known. Commercially available mixtures of primary mono-alkanols prepared via the oligomerization of ethylene and the hydroformylation or oxidation and hydrolysis of the resulting higher olefins are particularly preferred.

Examples of commercially available alkanol mixtures include the NEODOL alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ aldanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Proctor and Gamble Company and the TA alchohols of Ashland Oil Company.

The term "stable free radical nitroxide" as used herein shall mean a free radical nitroxide that can be prepared by conventional chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of alkanols to the corresponding aldehydes. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

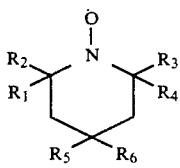

wherein each of $R_1$, $R_2$, $R_3$ and $R_4$ is an alkyl, aryl or heteroatom substituted alkyl group having 1 to about 15 carbon atoms and no hydrogen is bound to the remaining valences on the carbon atoms bound to the nitrogen, and each of $R_5$ and $R_6$ is alky, hydrogen, aryl or a substituted hexeroatom. As used herein, the term "alkyl" is meant to include cycloalkyl. The alkyl (or heteroatom substituted) groups $R_1$-$R_4$ may be the same or different, and preferably contain 1 to 15 carbon atoms. Preferably, $R_1$-$R_4$ are methyl, ethyl, or propyl groups. In addition to hydrogen, the heteroatom substituents may include, halogen, oxygen, nitrogen and the like. Preferably, one of $R_5$ and $R_6$ is hydrogen while the other is a heteroatom which does not interfere with the reaction. Suitable substituted heteroatoms include —OR,

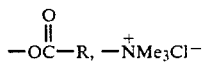

O—SO$_3$H, —O— polymer and the like.

In a preferred embodiment, the nitroxide is selected from the group consisting of 2,2,6,6- tetramethyl-piperidine-1-oxyl, 4-hydroxy-2,2,6, 6-tetramethyl-piperidine-1-oxyl, 4-oxo-2,2,6,6-tetramethyl-piperidient-1-oxyl, 2,2,6,6- tetramethyl-piperidine-1-oxyl-4-sulfate, 4-alkoxy-2,2,6,6-tetramethyl-piperidine-1oxyl and mixtures thereof, with 2,2,6,6-tetramethyl-piperidine-1-oxyl, 2,2,6,6-tetramethyl-piperidine1-oxyl-4-sulfate, and 4-alkoxy-2,2,6,6-tetramethyl-piperidine-1-oxyl being particularly preferred.

As used herein, the term "nitric acid" refers to nitric acid, fuming nitric acid or nitrous acid generated by contacting alkali metal nitrite with mineral acid. The nitric acid suitable for use in the present invention typically has a concentration in the range of from about 50 percent to about 100 percent, preferably about 70 percent. Generally, an amount of nitric acid in the range of from about 5 mole percent to about 100 mole percent, basis the number of moles of starting alkanol is used. If excess nitric acid is used and the reaction mixture becomes too acidic, the reaction stops. The nitric acid is typically added to the reaction mixture after all of the other reactants have been added. While not wishing to be bound by any particular theory, it is believed that nitrogen oxides (NO$_x$) are generated in the reaction and are the active species in the reaction.

The oxidants suitable for use in the instant invention are those compounds which are capable of oxidizing the stable free radical nitroxide to the oxoammonium salt. Suitable oxidants include oxygen or an oxygen-containing gas such as air. Whereas pure oxygen is preferred to accomplish the desired conversion, the oxygen can be diluted with an inert gas such as nitrogen, helium, argon, or other similar gas is also suitable. While air can be used as the oxidant, the reaction rate is much slower. For purposes of increasing the reaction rate, higher O$_2$ pressures such as, for example, 1000 psi can be utilized. In a preferred embodiment, pure oxygen is used as the oxidant and it is bubbled into the reaction solution. In another embodiment, air can be bubbled through the reaction solution.

The reaction in the present invention is carried out utilizing a solubilized free radical nitroxide, The solvent is generally a non-basic polar solvent (i.e., a solvent which does not form a strong complex with the oxoammonium ion) which is to a large extent miscible in water and in which the alkanol is readily soluble. While non polar solvents afford high conversions under comparable conditions of temperature, time and pressure, the use of non polar solvents results in undesirably high amounts of aldehyde dimerization products. Basic polar solvents have a tendency to shut down the reaction, thus resulting in incomplete conversions. Polar solvents which are most suitable are those which are inert in the reaction. The solvent may be added to the reaction mixture, or alternatively, the nitroxide may be dissolved in the solvent prior to addition of the nitroxide to the reaction medium. The solvent is typically selected from the group consisting of acetonitrile, sulfolane, tertiary alcohols such as tertiary butyl alcohol, and mixtures thereof. In a preferred embodiment, the solvent is acetonitrile. The amount of solvent utilized in the process is typically in the range of from about 20:1 to about 0.5:1, preferably from about 10:1 to about 5:1, basis the weight of the starting alkanol.

The amounts and concentrations of the reactants utilized in the process of the instant invention can vary within wide ranges. The amount of stable free radical nitroxide is typically in the range of from about 1 mole percent by weight to about 50 mole percent, preferably from about 5 mole percent by weight to about 20 percent, basis the number of moles of starting alkanol. Generally, the amount of nitric acid is in the range of from about 5 mole percent to about 100 mole percent, preferably from about 25 mole percent to about 50 mole percent, basis the number of moles of the starting alkanol.

The process of the present invention is typically conducted under mild conditions, with good results being obtained using a temperature in the range of from about $-10°$ C. to about 25° C., and preferably in the range of from about 10° C. to about 20° C. Reaction pressures are not critical although higher pressures result in increased reaction rates. Pressures in the range of from about atmospheric pressure up to about 1000 psig can be employed with good results. The time of reaction required in order to obtain a high selectivity to aldehydes is typically about eight hours or less. The time in which the reaction proceeds to aldehydes may, however, be longer in the event that basic solvents such as acetone, dimethylformanide, and N-methyl pyrrolidone are used. The optimum times of maximizing the selectivity to aldehydes using a particular solvent can be readily determined by one skilled in the art with a minimal amount of routine experimentation.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.032 moles of alkanol, 0.006 moles of the nitroxide, and solvent may be added to the reaction vessel, followed by the addition of 0.016 moles of 70 percent nitric acid and bubbling $O_2$ through the reaction mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. The reaction product can be purified by a number of conventional means such as, for example, distillation.

Depending upon process conditions and the nitroxide used, the selectivity to aldehydes obtained by this invention can be greater than about 95% of starting alkanol material being converted. The products produced by the instant process can be used in a variety of applications. For example, these products can be used as intermediates in the preparation of esters, imides, imines, amines and acids.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

Example 1

6 Grams of 1-dodecanol, 1 gram of 2,2,6,6-tetramethylpiperidine-1-oxyl, 25 milliliters of acetonitrile and 1 gram of 70% nitric acid were charged to a 100 milliliter round bottomed flask. An $O_2$ stream was then bubbled through the mixture. The reaction temperature was held at 10° C. over an 8 hour period. The results are presented in Table I.

EXAMPLE 2

6 Grams of 1-dodecanol, 1 gram of 2,2,6,6-tetramethylpiperidine-1-oxyl, 25 milliliters of tertiary butyl alcohol, 1 gram of 70% nitric acid and 2 grams of water were charged to a 100 milliliter round bottomed flask. A stream of air was then bubbled through the mixture. The reaction temperature was held at 0°C. over a 3 hour period. The results are presented in Table I.

Example 3

6 Grams of 1-dodecanol, 1 gram of 2,2,6,6- tetramethylpiperidine-1- oxyl, 25 milliliters of glyme, and 1 gram of 70% nitric acid were charged to a 100 milliliter round bottomed flask. An $O_2$ stream was then bubbled through the mixture. The reaction temperature was held at 10° C. over a 6 hour period. The results are presented in Table I.

Comparative Example A

Comparative Example A was carried out in a manner similar to Example 1 except that the temperature was held at 35° C. for six hours. The results are presented in Table I.

Comparative Example B

Comparative Example B was carried out in a manner similar to Example 1 except that the reaction temperature wall allowed to warm to 23° C. over an additional 16 hour period. The results are presented in Table I.

As can be seen in Table I, temperatures exceeding 25° C or highly extended reaction times, i.e., times greater than about 8 hours, afford carboxylic acids rather than the desired aldehydes.

TABLE I

Oxidation Of Alkanols to Aldehydes

| | % Conversion | % Sel. Aldehydes | % Sel. Esters + Heavies | % Sel. Acids |
|---|---|---|---|---|
| Example 1 | 72 | >99.9 | <0.1 | 0 |
| Example 2 | 24 | >99 | <1 | 0 |
| Example 3 | 34 | >99 | <1 | <1 |
| Comparative Example A | >99.9 | 33 | 3 | 64 |
| Comparative Example B | 96 | 22 | 2 | 76 |

What is claimed is:

1. A process for the preparation of an aldehyde which comprises reacting the corresponding alkanol having a carbon number in the range of from about 1 to about 45 with a solubilized stable free radical nitroxide having the formula:

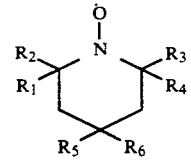

wherein each of $R_1$, $R_2$, $R_3$ and $R_4$ is an alkyl, aryl or heteroatom substituted alkyl group having 1 to about 15 carbon atoms and each of $R_5$ and $R_6$ is alky, hydrogen, aryl or a substituted heteroatom, nitric acid and an non-basic polar solvent selected from the group consisting of acetonitrile, sulfolane, tertiary butyl alcohol, tertiaryl amyl alcohol, and mixtures thereof, in the presence of an oxygen-containing gas, for about eight hours or less at a temperature in the range of from about −10° C. to about 25° C., and thereafter separating out the aldehyde.

2. The process of claim 1 wherein the solubilized stable free radical nitroxide is selected from the group consisting of 2,2,6,6-tetramethyl-piperidine-1-oxyl, 4-hydroxy-2,2,6,6- tetramethyl-piperidine-1-oxyl, 4-oxo-2,2,6,6-tetramethyl-piperidine-1-oxyl, 2,2,6,6- tetramethyl-piperidine-1-oxyl-4-sulfate, 4-alkoxy-2,26,6-tetramethyl-piperidine-1-oxyl and mixtures thereof.

3. The process of claim 2 wherein the solubilized stable free radical nitroxide is selected from the group consisting of 2,2,6,6- tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

4. The process of claim 1 wherein said solvent is acetonitrile.

5. The process of claim 1 wherein said is nitric acid has a concentration in the range of from about 50 percent to about 100 percent.

6. The process of claim 5 wherein said nitric acid has a concentration of about 70 percent.

7. The process of claim 1 wherein said the amount of nitric acid utilized is in the range of from about 5 mole percent to about 100 mole percent.

8. The process of claim 1 wherein said alkanol is contacted with said solubilized stable free radical nitroxide, followed by the addition thereto of said nitric acid and said oxidant.

9. The process of claim 8 wherein the amount of solubilized stable free radical nitroxide is in the range of from about 1 mole percent to about 50 mole percent, basis the number of moles of said alkanol.

10. The process of claim 8 wherein the amount of solubilized stable free radical nitroxide is in the range of from 5 mole percent to about 20 mole percent, basis the number of moles of said alkanol.

11. The process of claim 8 wherein said the amount of nitric acid utilized is in the range of from about 5 mole percent to about 100 mole percent.

12. The process of claim 1 wherein said oxygen-containing gas is selected from pure oxygen and oxygen in air.

13. The process of claim 12 wherein said oxygen-containing gas is pure oxygen.

14. The process of claim 1 wherein said process is carried out at a temperature in the range of from about 10° C. to about 20° C. and at atmospheric pressure.

* * * * *